(12) United States Patent
Sutton et al.

(10) Patent No.: US 7,531,002 B2
(45) Date of Patent: May 12, 2009

(54) INTERVERTEBRAL DISC WITH MONITORING AND ADJUSTING CAPABILITIES

(75) Inventors: Jeffrey Karl Sutton, Medway, MA (US); Edward John Crowe, Cohasset, MA (US); Kristy Lynn Davis, Smithfield, RI (US); Michael O'Neil, West Barnstable, RI (US); Richard Pellegrino, Upton, MA (US); Hassan Serhan, Easton, MA (US)

(73) Assignee: Depuy Spine, Inc., Raynham, MA (US)

( * ) Notice: Subject to any disclaimer, the term of this patent is extended or adjusted under 35 U.S.C. 154(b) by 361 days.

(21) Appl. No.: 10/826,186

(22) Filed: Apr. 16, 2004

(65) Prior Publication Data

US 2005/0234555 A1   Oct. 20, 2005

(51) Int. Cl.
    *A61F 2/44*   (2006.01)
(52) U.S. Cl. ............. 623/17.15; 623/18.12; 623/23.47; 606/90
(58) Field of Classification Search ............. 623/17.15, 623/18.12, 23.47; 606/90, 102
    See application file for complete search history.

(56) References Cited

U.S. PATENT DOCUMENTS

| | | | |
|---|---|---|---|
| 4,759,766 A | 7/1988 | Buettner-Janz | |
| 5,314,477 A | 5/1994 | Marnay | |
| 5,445,008 A | 8/1995 | Wachter | |
| 5,556,431 A | 9/1996 | Buttner-Janz | |
| 5,674,296 A | 10/1997 | Bryan | |
| 5,719,324 A | 2/1998 | Thundat | |
| 6,016,686 A | 1/2000 | Thundat | |
| 6,045,579 A * | 4/2000 | Hochshuler et al. | 623/17.16 |
| 6,050,722 A | 4/2000 | Thundat | |
| 6,096,559 A | 8/2000 | Thundat | |
| 6,118,124 A | 9/2000 | Thundat | |
| 6,167,748 B1 | 1/2001 | Britton, Jr. | |
| 6,190,414 B1 * | 2/2001 | Young et al. | 623/17.15 |
| 6,212,939 B1 | 4/2001 | Thundat | |
| 6,263,736 B1 | 7/2001 | Thundat | |
| 6,289,717 B1 | 9/2001 | Thundat | |
| 6,311,549 B1 | 11/2001 | Thundat | |
| 6,311,557 B1 | 11/2001 | Davis | |
| 6,336,366 B1 | 1/2002 | Thundat | |
| 6,352,524 B1 | 3/2002 | Bunt | |
| 6,447,448 B1 | 9/2002 | Ishikawa | |
| 6,454,806 B1 * | 9/2002 | Cohen et al. | 623/17.15 |
| 6,464,346 B2 | 10/2002 | Otis | |
| 6,475,639 B2 | 11/2002 | Shahinpoor | |
| 2001/0028036 A1 | 10/2001 | Thundat | |
| 2002/0006682 A1 | 1/2002 | Benzel | |
| 2002/0039620 A1 | 4/2002 | Shahinpoor | |
| 2002/0139171 A1 | 10/2002 | Benzel | |
| 2002/0170875 A1 | 11/2002 | Benzel | |
| 2002/0174724 A1 | 11/2002 | Benzel | |
| 2003/0028036 A1 | 2/2003 | Canali | |

(Continued)

OTHER PUBLICATIONS

Roy, Neurosurgery, Microelectromechanical systems and neurosurgery: a new era in a new millennium, Neurosurgery, 2001, pp. 779-797, vol. 49, Issue 4.

*Primary Examiner*—David Isabella
*Assistant Examiner*—J. G. B.
(74) *Attorney, Agent, or Firm*—Thomas M. DiMauro

(57) ABSTRACT

A prosthetic endplate having articulation surfaces whose relative positions can be post-operatively adjusted.

10 Claims, 13 Drawing Sheets

U.S. PATENT DOCUMENTS

| | | |
|---|---|---|
| 2003/0062579 A1 | 4/2003 | Benzel |
| 2003/0116813 A1 | 6/2003 | Benzel |
| 2004/0021184 A1 | 2/2004 | Benzel |
| 2005/0256576 A1 | 11/2005 | Moskowitz |

* cited by examiner

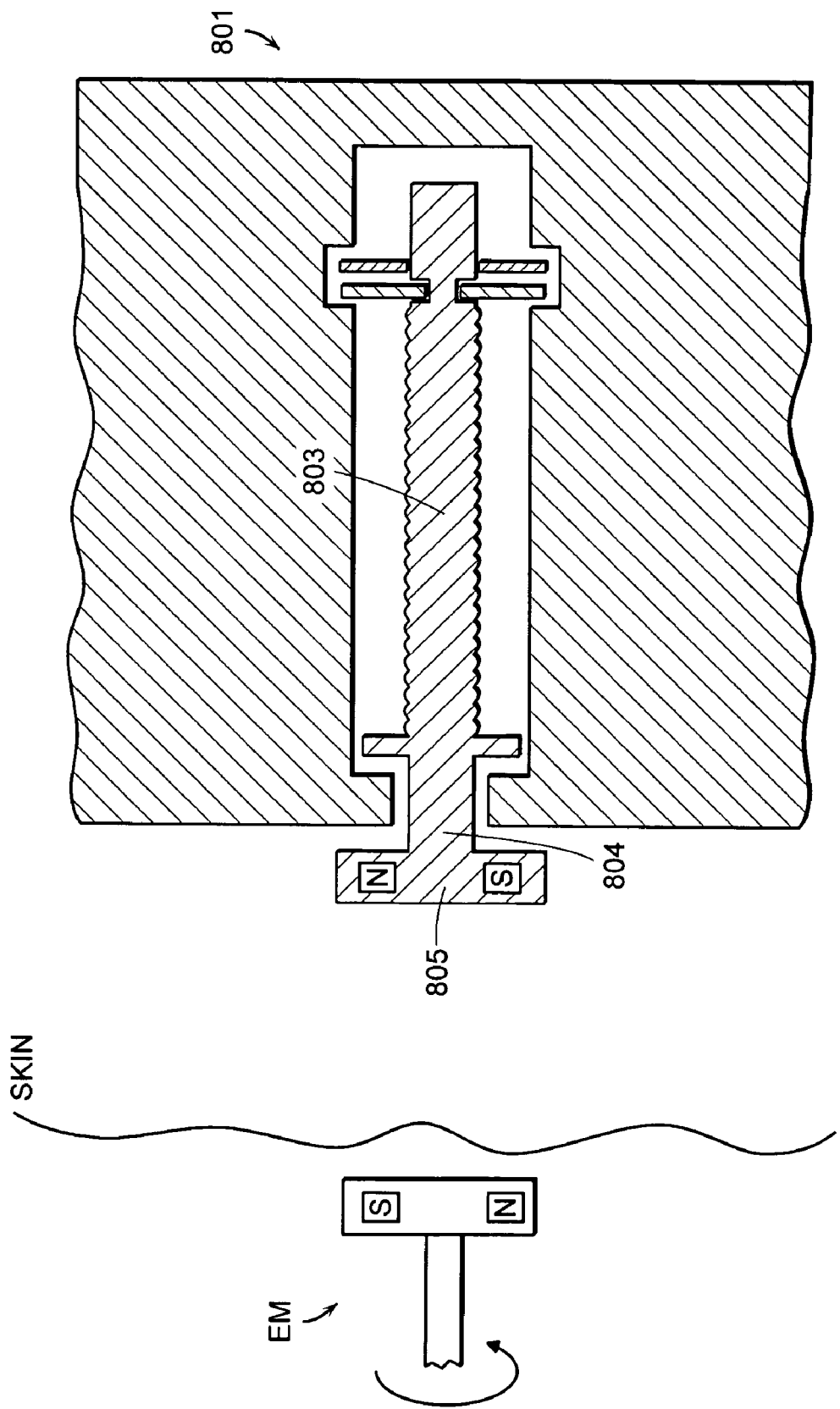

INTERVERTEBRAL DISC WITH MONITORING AND ADJUSTING CAPABILITIES

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

U.S. Pat. No. 4,759,766 ("Buttner-Janz") discloses one such motion device comprising three components: an inferior endplate, a superior endplate, and a core having two articulation interfaces. Both the inferior and superior endplates have raised bosses with concave spherical articulation surfaces in the center. The core has convex surfaces on both the top and bottom that are surrounded by raised rims. The articulation surfaces of the core are designed to articulate with the articulation surfaces of the endplates. A cross-section of this device is shown in FIG. 13.

Because articulating motion discs such as those described in Buttner-Janz seek to mimic the natural motion of the natural disc, it is desirable to place the disc at the precise location whereby the disc will have a center of rotation precisely equal to that of the natural disc. Accordingly, the device must be precisely placed at a predetermined spot during implantation in order mimic the natural center of rotation. However, it has been found that this is difficult to do in practice due to the limited visibility and space of the surgical field. For example, it has been reported that as much as 33% of the such discs are positioned at least 2 mm too anterior within the disc space. In addition, device movement may occur post operatively due to inadequate tissue adherence or trauma.

Although the surgeon can select a revision surgery to re-position the motion disc, such a surgery is costly and typically painful to the patient, and may include a risk of morbidity. Accordingly, it is an object of the present invention to allow post-implantation selective adjustment of the center of rotation of the articulating motion disc without requiring a revision surgery.

SUMMARY OF THE INVENTION

The present inventors have developed a device for adjusting the center of rotation of an articulating motion, wherein each prosthetic endplate has an outer plate adapted for fixation to bone, and a lower plate adapted for articulation, and includes a means for selectively adjusting a relative position of the inner plate upon the outer plate. The selective adjustment of the inner plate relative to the outer plate (which remains fixed upon the bone) allows the center of rotation (COR) to be desirably adjusted.

The device of the present invention provides particular advantage because it allows the surgeon to post-operatively reset the COR of the device without having to perform a revision surgery.

Therefore, in accordance with the present invention, there is provided a prosthetic endplate in an intervertebral motion disc having an anterior end and a posterior end, the endplate comprising:

i) an outer plate comprising
   an outer surface adapted for fixation to a first vertebral body,
   an inner surface, and
   a body portion therebetween,
ii) an inner plate comprising
   an inner surface having a first articulation surface,
   an outer surface, and
   a body portion therebetween,
iii) means for selectively adjusting a relative position of the inner plate upon the outer plate.

There is also provided a method of adjusting a position of a prosthetic endplate, comprising the steps of:
a) providing a prosthetic endplate in an intervertebral motion disc having an anterior end and a posterior end, the endplate comprising:
  i) an outer plate comprising:
    an outer surface adapted for fixation to a first vertebral body,
    an inner surface, and
    a body portion therebetween,
  ii) an inner plate comprising:
    an inner surface having a first articulation surface,
    an outer surface, and
    a body portion therebetween,
b) fixing the outer surface of the outer plate to the first vertebral body to produce a first relative position of the inner plate upon the outer plate, and
c) selectively adjusting the first relative position to a second relative position of the inner plate upon the outer plate.

In some especially preferred embodiments, the means for providing selected adjustment of the motion disc includes magnetism or telemetry, whereby the physician can determine and adjust the center of rotation of the disc on a completely non-invasive manner.

These adjustments can be made based upon post-operative imaging results, as well as sensor-based determinations of distance or load indicating device mal-placement or movement and patient feedback.

Adjustment can be pre-programmed into the disc-based sensors for self activation to ensure desired the COR placement.

DESCRIPTION OF THE FIGURES

FIG. 3b is an axial view of the locking mechanism of FIG. 3a.

FIG. 7b is a side view of a portion of the endplate of FIG. 7a.

FIG. 8 is a cross-section of an implanted inner plate, wherein the captured screw has a magnetic proximal end portion.

DETAILED DESCRIPTION OF THE INVENTION

Figure 1A:
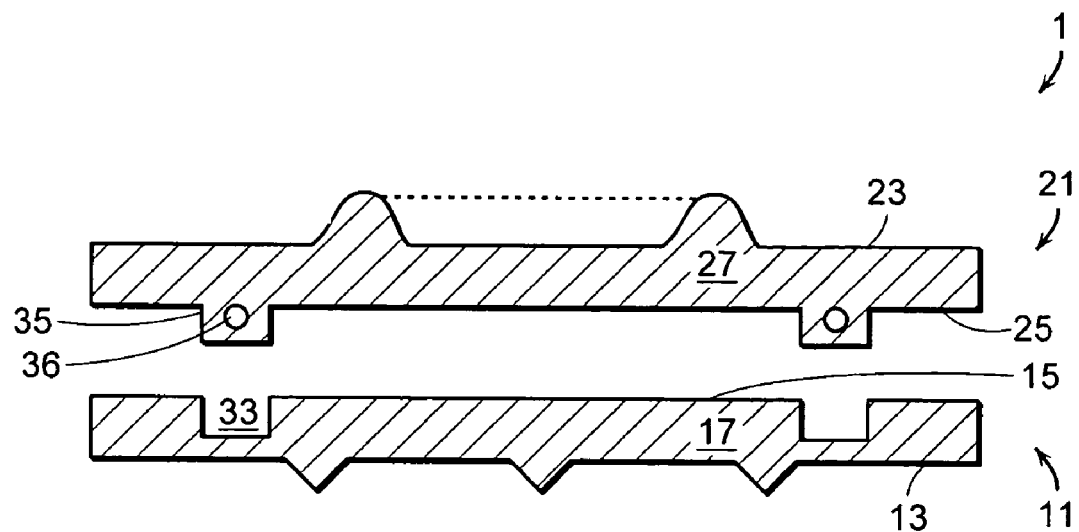
FIG. 1a is an exploded cross-section of a first embodiment of an endplate of the present invention wherein the inner surfaces have a recess and projection.
Figure 1B:
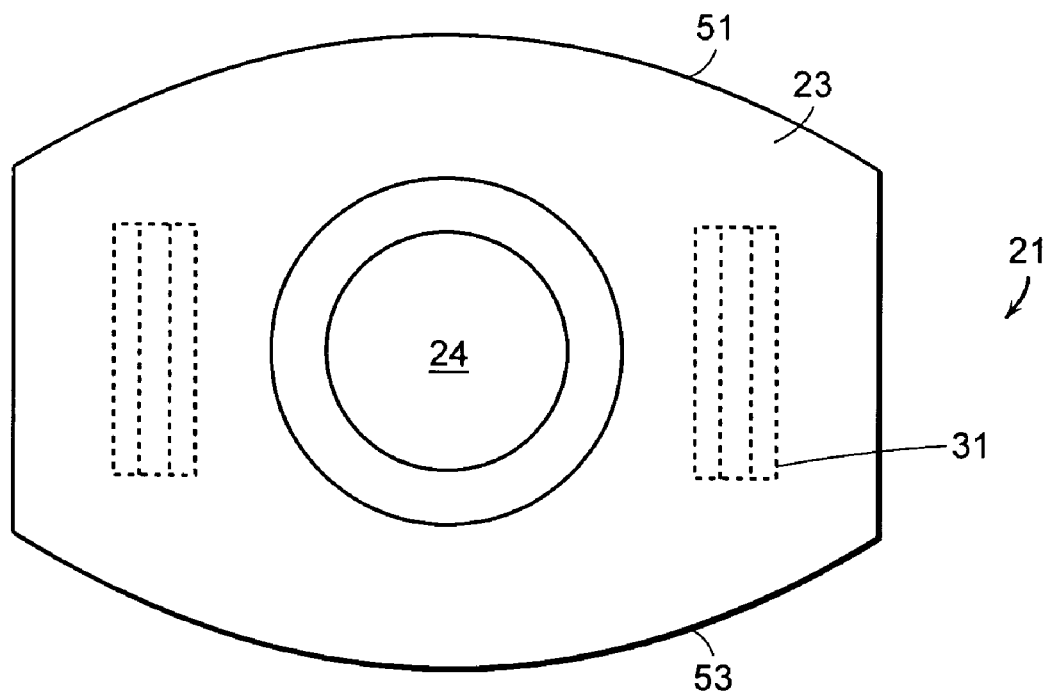
FIG. 1b is a top view of the first embodiment of an inner plate of the present invention.
Figure 1C:
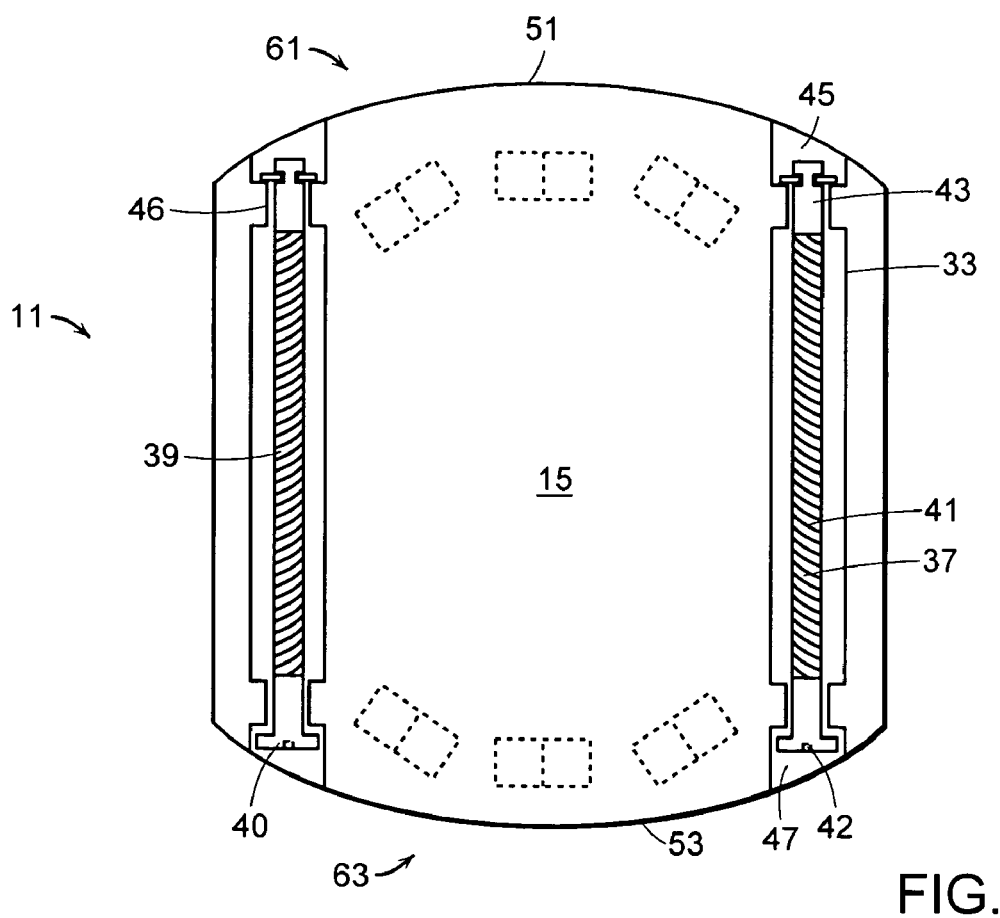
FIG. 1c is a top view of the outer plate of the first embodiment of the present invention, as viewed from the inner plate.
Figure 1D:
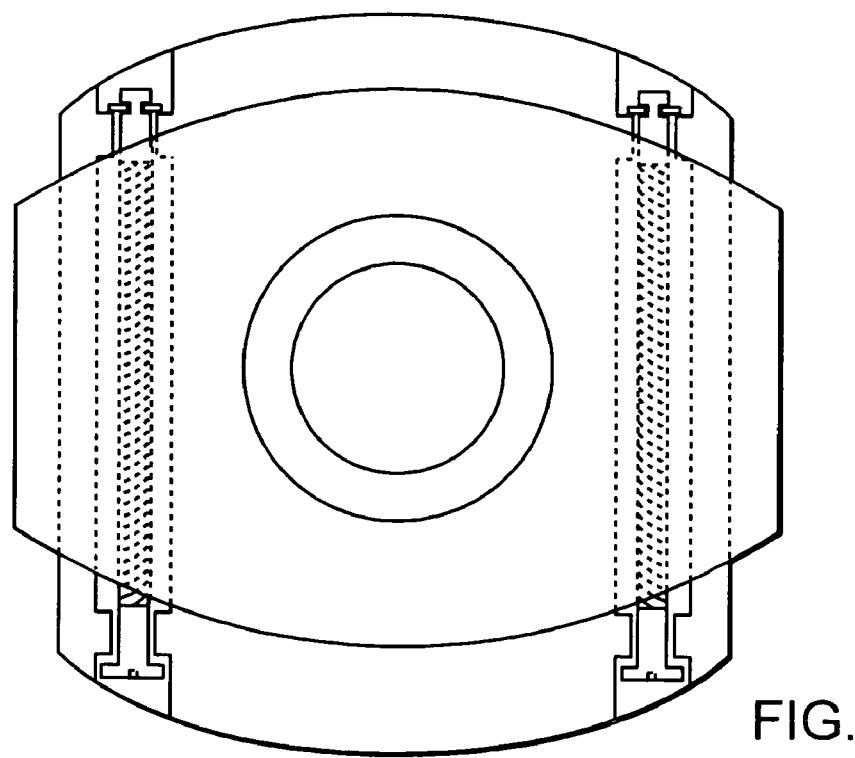
FIG. 1d is a top view of the first embodiment of the present invention, wherein the inner plate rests upon the outer plate.

Now referring to FIGS. 1a-1d, there is provided a prosthetic endplate 1 in an intervertebral motion disc having an anterior end and a posterior end, the endplate comprising:
i) an outer plate 11 having an anterior end 61 and a posterior end 63, and comprising
an outer surface 13 adapted for fixation to a first vertebral body,
an inner surface 15 having an anterior end 51 and a posterior end 53, and
a body portion 17 therebetween,
ii) an inner plate 21 having an anterior end 51 and a posterior end 53, and comprising
an inner surface 23 having a first articulation surface 24,
an outer surface 25, and
a body portion 27 therebetween,
iii) means for selectively adjusting a relative position of the inner plate upon the outer plate.

In this particular embodiment, the means is disposed upon the inner surfaces and comprises an elongated channel 33 and an elongated projection 35 adapted to mate with the elongated recess. A bore 36 is formed in the projection and runs the length of the projection, opening upon both the anterior and posterior ends of the projection. The interior surface of the bore is threaded. Disposed within recess 33 of the outer plate is a captured screw 37 having an outer thread adapted to mate with the thread of the bore. This screw comprises a longitudinal shaft 39 having a thread 41 thereon, a blunt distal tip 43, and a proximal head 40 having a slot 42. Since both the blunt distal tip and the head ends of the captured screw are respectively seated in an anterior recess 45 and a posterior recess 47 defined by necks 46 of the outer plate, the capture renders the captured screw spatially fixed (save rotation). Rotation of the captured screw bites into the threaded bore of the other plate (which is not fixed), thereby causing relative movement of the inner plate to move in the A-P direction, thereby affecting a saggital re-alignment.

Figure 2:
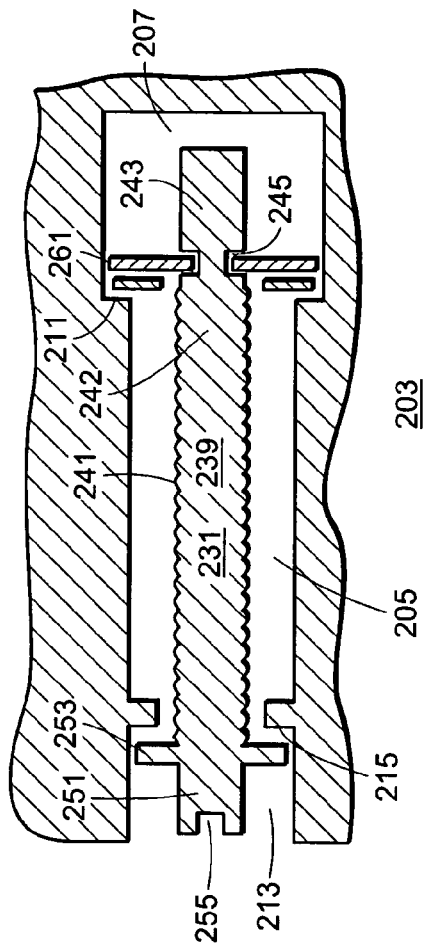
FIG. 2 is a cross-section of a portion of an outer plate of the present invention having a captured screw.

Now referring to FIG. 2, in preferred embodiments, the screws are captured so that they are contained within one of the plates and limited to rotational movement only.

In this particular embodiment, there is provided:
a) an outer plate portion 201 having an inner surface 203 having a longitudinal channel 205 therein, the channel having an anterior end portion 207 forming an anterior shoulder 211, and a posterior end portion 213 having a shoulder 215;
b) a captured screw 231 having a longitudinal shaft 239 having a thread 241 thereon, an anterior portion 242 having a blunt tip 243 and a circumferential recess 245, and a posterior portion 251 having a circumferential projection 253 and an axial slot 255;
c) an annular clip 261 disposed about the circumferential recess of the screw, and
d) an annular washer 263 disposed about the shaft of the screw and between the annular clip and the anterior shoulder.

In this embodiment, capture of the screw is achieved by providing anterior and posterior shoulder on the mating plate. Anterior movement of the screw will cause annular clip to contact the anterior shoulder (thereby preventing movement in the anterior direction). Posterior movement of the screw will cause the posterior circumferential projection to contact the posterior shoulder (thereby preventing movement in the posterior direction). In some embodiments, a circle clip replaces the snap ring.

In some embodiments, the captured screw comprises a head selected from the group consisting of a slotted head, an Allen head, a Torx$^R$ head, a Phillips head, and a Robertson$^R$ head.

Although in the above embodiments, the elongated channel is disposed upon the outer plate and the elongated projection is disposed upon the inner plate, in other embodiments, these features are switched, wherein the elongated channel is disposed upon the inner plate and the elongated projection is disposed upon the outer plate.

It may also be desirable to have a mechanism to prevent unwanted rotation of the screws during normal use and life of the device.

In some embodiments, unwanted rotation is provided by providing a high friction coefficient upon the screw-seat interface. In such situations, rotation of the screw is effected only by the imposing of an extremely high force, such as that provided by a magnet.

Figure 3B:
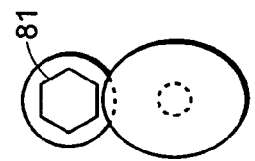
Figure 3A:
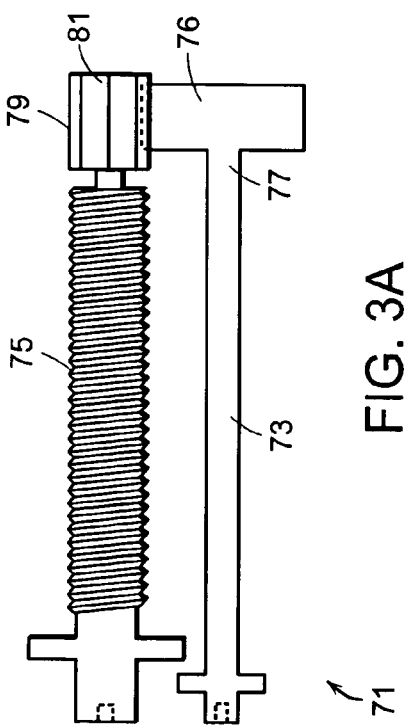
FIG. 3a is a side view of a cam-type locking mechanism of the present invention.

In other embodiments, a locking mechanism is provided that is easily accessed and disabled by the surgeon using a posterior or postero-lateral approach to perform adjustments when necessary. Now referring to FIGS. 3a and 3b, in one embodiment, the locking mechanism 71 comprises a shaft 73 disposed alongside the screw 75, wherein the shaft has an elliptical cam 76 disposed on an end 77 of a cam shaft. The cam is designed to contact an end 79 of the screw (or, a portion of the screw near its end) so that, when the cam is in its locking position, it exerts a force on the screw, thereby preventing rotation of the screw. The region of the screw that the cam contacts may be augmented by one or more flats 81 designed to enhance the locking force of the contacting cam. When locking is no longer desired (such as when the surgeon desires to re-align the COR), the surgeon rotates the cam to disengage the cam from the screw.

Figure 4:
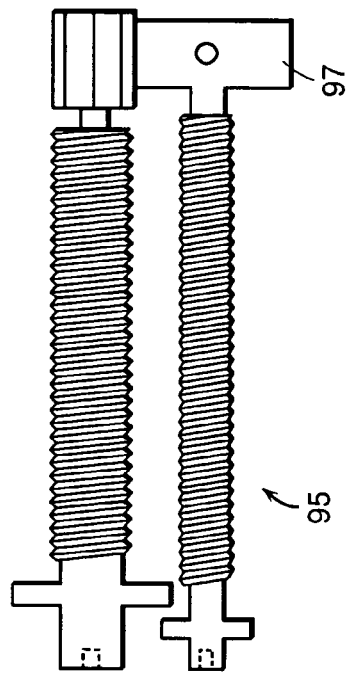
FIG. 4 is a side view of a threaded shaft-type locking mechanism of the present invention.

Now referring to FIG. 4, in some embodiments, the locking mechanism 85 can comprise a threaded shaft 87 having a tapered end 89 adapted to engage and lock a flat spot 91 of the screw 93.

Figure 5A:
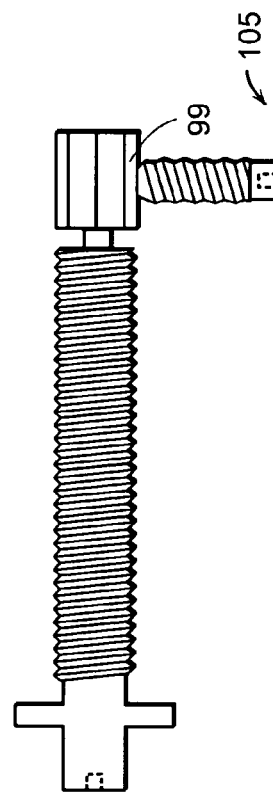
FIG. 5a displays a hinged lever-type locking mechanism of the present invention in its locked position.
Figure 5B:
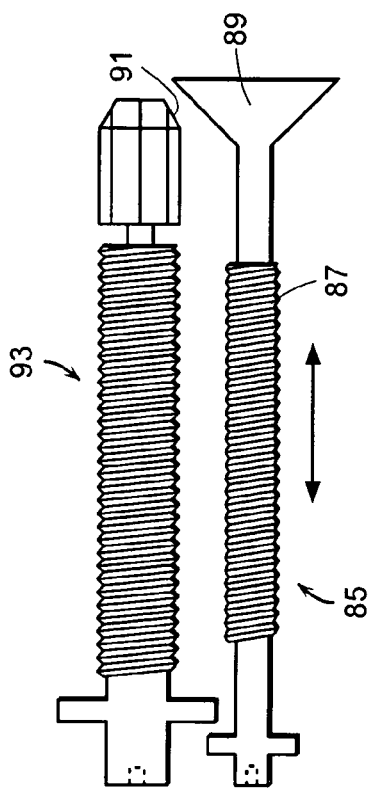
FIG. 5b displays a hinged lever-type locking mechanism of the present invention in its disengaged position.

Now referring to FIGS. 5a and 5b, in some embodiments, the locking mechanism 95 can comprise a hinged lever 97 adapted to engage flat spots 99 of the screw. FIG. 5a displays the hinged lever in its locked position, while FIG. 5b displays the hinged lever is its disengaged position.

Figure 6:
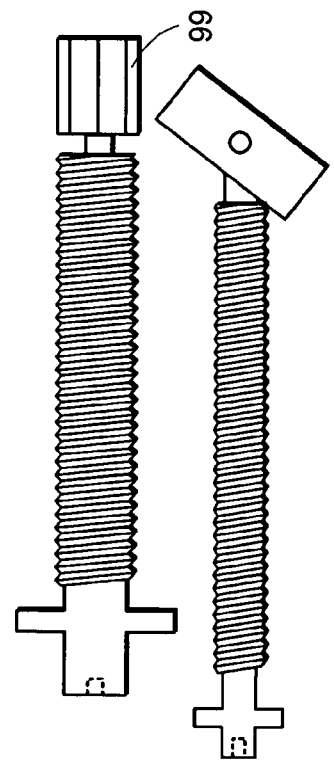
FIG. 6 displays a screw-type locking mechanism of the present invention in its disengaged position.

Now referring to FIG. 6., in some embodiments, the locking mechanism 105 can comprise a screw, such as a set screw, adapted to engage flat spots 99 of the screw.

In FIGS. 3A, 4, 5A, 5B and 6, the locking screw may comprise a head selected from the group consisting of a slotted head, an Allen head, a Torx$^R$ head, a Phillips head, and a Robertson$^R$ head.

In some embodiments, the captured screw and mating bore have conventional mating threads whereby a clockwise turn of the screw will cause the inner plate to move anteriorly (relatively to the fixed outer plate), and a counter-clockwise turn of the screw will cause the inner plate to move posteriorly (relatively to the fixed outer plate). Accordingly, the device of the present invention allows the physician to repeatedly adjust the COR of the device.

In some embodiments, the implant includes a measuring means associated with the captured screw, wherein the measuring means is adapted to measure the distance change provided by actuation of the capture screw. This measuring means allows the surgeon to understand exactly how much adjustment has been made by actuation of the captured screw. In some embodiments, the measuring means is adapted to provide incremental stops of the captured screw during rotation.

In this particular embodiment, the means 31 includes first and second captured screws. Having a pair of screws is advantageous because the pair provides additional strength (in comparison to a single screw) as well as redundancy, thereby enhancing the safety of the system.

In other embodiments, the means 31 includes a single captured screws. Having a single captured screw is advantageous because the physician need only make a single adjustment in order to re-adjust the COR. If the physician makes the adjustment percutaneously, only a single invasive procedure is required. If the physician makes the adjustment telemetrically, there is no concern that the signal will effect different selective adjustments to the plurality of screws.

In other embodiments (not shown), the elongated channel-projection combination is adapted so that the elongations runs in the medial-lateral direction. In this embodiment, adjustment of the captured screw results in a medial-lateral adjustment of the articulation surface relative to the outer plate.

Figure 7A:
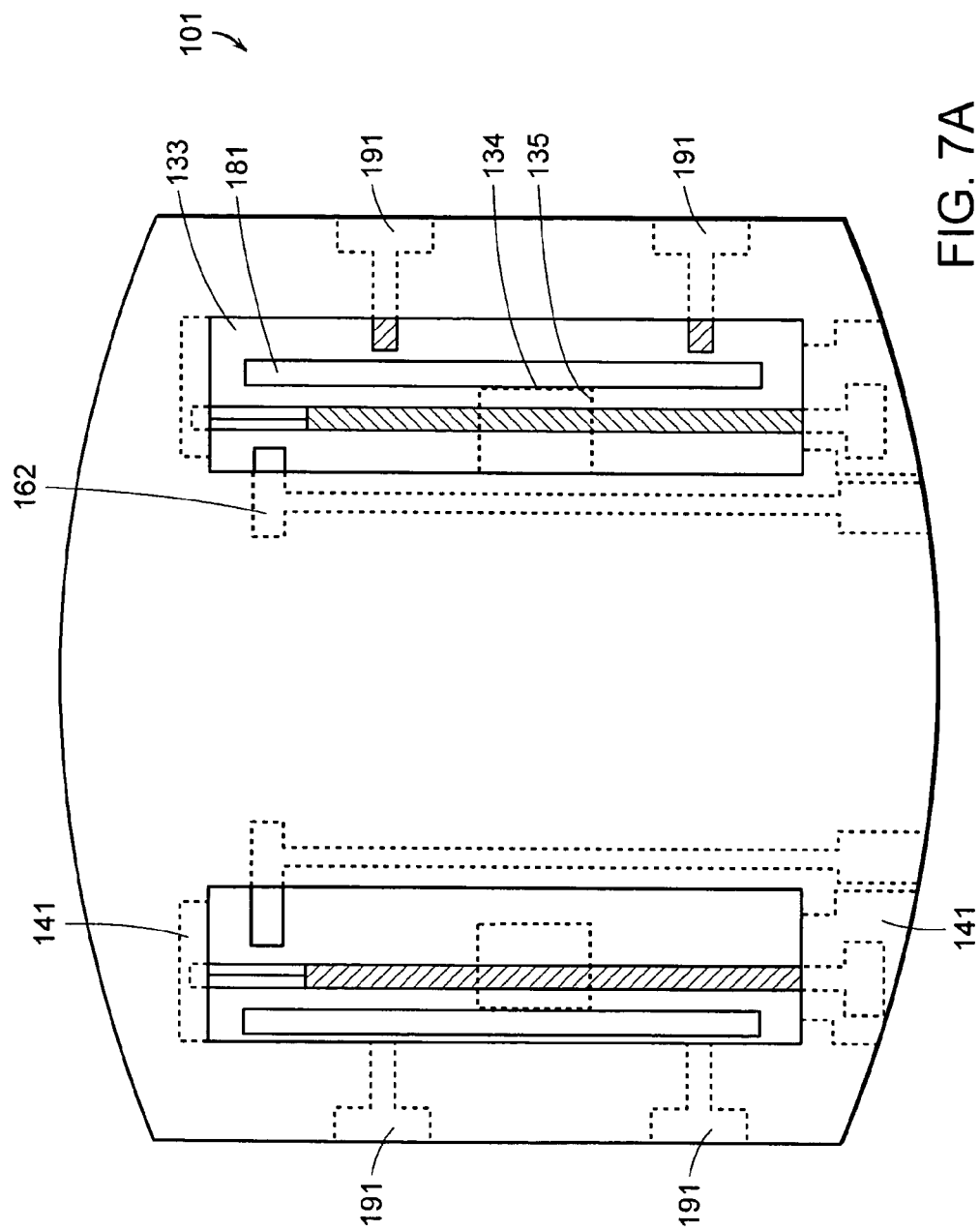
FIG. 7a is an embodiment of the present invention capable of achieving both saggital and lateral re-alignment.

In another embodiment of the present invention, there is provided a prosthetic endplate that is adapted to achieve not only saggital re-alignment, but also lateral re-adjustment. Now referring to FIG. 7a, there is provided an end plate 101 of the present invention wherein the channels 133 in the outer plate 111 are somewhat wider than the corresponding projections 135 (shown as a dotted line) in the inner plate, and the terminal recesses 141 adapted for capturing the captured screw are also laterally elongated to accommodate lateral movement of the captured screws. Moreover, the endplate further comprises:

a) a pair of moveable plates 181, each plate disposed within a corresponding channel and abutting (and preferably affixed to) a side wall 134 of the corresponding projection 135, and b) opposed pairs of screw means 191 adapted to contact a moveable plate 181 disposed in each recess.

In use, rotating the screw means alters the lateral position of the moveable plate, thereby urging the corresponding projection to a new lateral position.

Figure 7B:
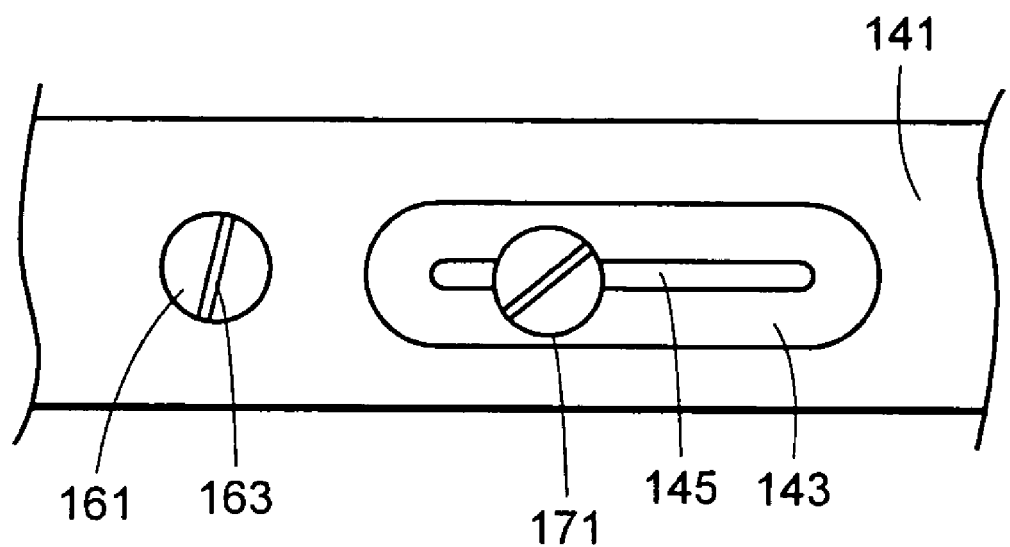

Now referring to FIG. 7b, there is provided a side view of a portion of the endplate in which the proximal ends of each of a locking mechanism 161 comprising cam 162 and a captured screw 171 are housed. The cam 161 has a slot 163 for reception of a screwdriver. Rotation of the cam 161 permits locking or unlocking of the corresponding moveable plate. Terminal recess 141 has a shoulder 143 forming a laterally elongated slot 145 for laterally slidable reception of the proximal portion of the captured screw. Lateral movement of the captured screw allows medial-lateral (saggital) repositioning of the inner plate vis-vis the outer plate. Rotation of the captured screw 171 permits axial movement of the corresponding inner plate.

In some embodiments, the adjustment of the relative positions of the inner and outer plates is accomplished by percutaneous actuation. In some embodiments thereof, the means for selective adjustment includes at least one captured screw having a slotted head adapted for reception of a screwdriver. In preferred embodiments thereof, the means for selective adjustment includes at least one captured screw having a slotted head, an Allen head, a Torx$^R$ head, a Phillips head, and a Robertson$^R$ head. In use, a surgeon who desires post-surgical adjustment can access the screw head by a percutaneous posterior approach through the annulus. Rotation of the screw would cause the inner plate to move relative to the fixed outer plate, thereby affecting correction of the COR.

In some embodiments, COR adjustment is affected by the use of a powerful external magnet. In one embodiment thereof, and now referring to FIG. 8, the inner endplate 801 comprises a captured screw 803 having a posterior end portion 804 defining a terminal magnetic nut 805 having north N and south S poles. In use, a powerful external magnet EM is placed near or on the patient's skin SKIN in the vicinity of the prosthetic endplate and rotated a predetermined amount. The attractive-repulsive force produced between the external magnet and the magnetic nut is sufficient to effectuate rotation of the captured screw in a predetermined amount. As above, rotation of the captured screw causes relative movement in the inner plate in relation to the fixed outer plate, thereby adjustment the COR.

In some embodiments, the selected magnet comprises a rare earth metal. In other embodiments, the selected magnet is an electromagnet.

Figure 9:
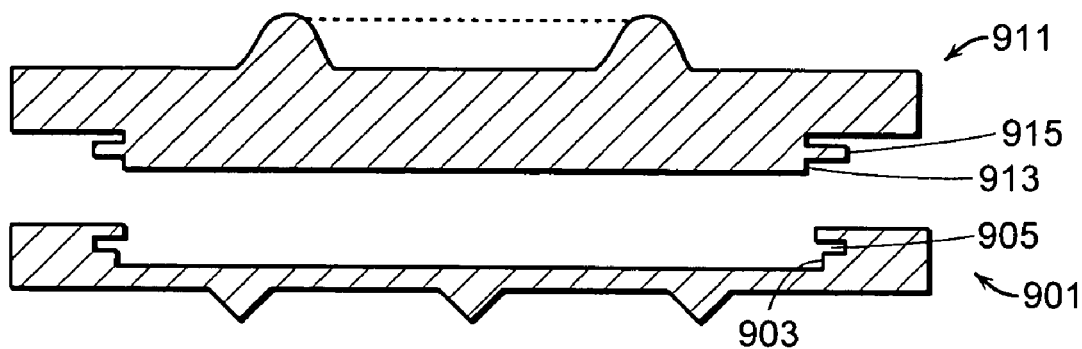
FIG. 9 is a cross-section of an embodiment of the present invention wherein the channel and projection combination is disposed upon the respective side surfaces of the outer and inner plates.

In other embodiments, and now referring to FIG. 9, the channel and projection combination that provides for relative movement is disposed upon the respective side surfaces of the outer and inner plates. In particular, the side surface 903 of the outer plate 901 has a pair of elongated channels 905, while the side surfaces 913 of the inner plate 911 have a corresponding pair of projections 915 designed to mate the with the recesses.

Figure 10:
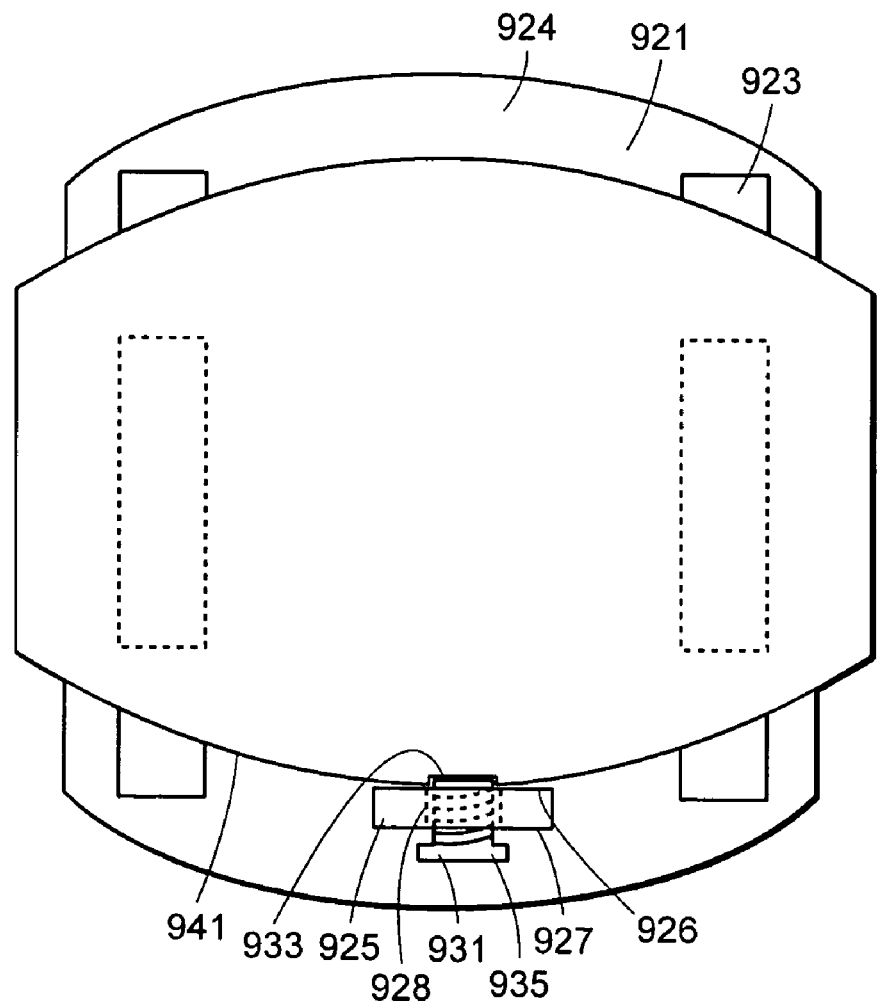
FIG. 10 is a top view of an embodiment wherein the captured screw pushes against a side surface of the inner plate.

In other embodiments, and now referring to FIG. 10, the captured screw 931 can be disposed on one end side of the inner plate. In particular embodiment, the outer endplate comprising channels 923 and inner surface 924 further comprises a projection 925 extending from the inner surface and having an anterior surface 926, a posterior surface 927, and an anterior-posterior threaded through-hole 928. The captured screw 931 is disposed in the threaded throughole and has a distal end 933 extending from the anterior surface of the projection and an proximal end 935 extending from the posterior surface of the projection. As above, clockwise rotation of the captured screw causes the distal end of the screw to push against the anterior side surface 941 of the inner plate, thereby providing relative movement of the inner plate in relation to the fixed outer plate, and thereby providing adjustment of the COR.

In some embodiments, the COR adjustment is carried out by the use of a motor. In one embodiment thereof (not shown), a motor having an externally extending rotor is affixed to the inner surface of the outer plate, and the rotor is axially connected to the proximal end of the captured screw. In use, an external Rf antenna is placed on the patient's skin in the vicinity of the prosthetic endplate and energy is sent to an internally-placed antenna (not shown). This internal antenna then provides the motor with an amount of energy required to the rotate the rotor in a predetermined amount. Rotation of the rotor effectuates rotation of the captured screw in a predetermined amount. As above, rotation of the captured screw causes relative movement in the inner plate in relation to the fixed outer plate, thereby adjustment the COR.

In some embodiments the COR adjustment is carried out by the use of a hydraulic means. In one embodiment thereof (not shown), there is provided i) a bag or bladder having an internal pressurized fluid and ii) a controllable valve communicating with an extended chamber affixed to the inner surface of the outer plate, wherein the bladder is connected to the proximal end of inner plate. In use, an external Rf antenna or other directable energy source is placed on the patient's skin in the vicinity of the prosthetic endplate and energy is sent to open the valve and release the pressurized liquid to the extended chamber (not shown). This chamber then expands and advances the inner plate to the predetermined amount based upon energy applied to increase valve opening or duration or fluid release.

In some embodiments, the COR adjustment is carried out by using thermoelectric nanomaterials that are adapted to store heat (in some cases, from the patient's body) and convert that heat into electricity to be used as a power source.

In the event that the actual surgery results in an acceptable positioning of the device, but a post-surgical shift occurs (for example, by adjacent level disc disease, trauma, injury or insufficient securement to the vertebral body) and produces a misalignment, the present invention can also be used to post-operatively adjust the center of rotation of the device.

The present invention may also allow the surgeon to adjust the relative positions of the components in order to optimize these relative positions based upon outcomes research that may appear in the literature after the disc has been implanted.

In some embodiments, the present invention further includes an implanted controller and an implanted sensor. These features may be easily adapted to provide automatic or closed loop adjustment of the COR of the device without the need for physician or surgical intervention.

In some embodiments, the implanted sensor is a force or pressure sensor adapted to provide information on load changes that occur as the patient is subjected to physical testing. This data can in turn be correlated back to and compared against the clinically desirable load balance in the saggital plane.

In some embodiments, the implanted sensor is located within the body of the endplate. In some embodiments, the implanted sensor is located within the core component.

Therefore, in some embodiments, there is provided an intervertebral motion disc comprising:

a) a prosthetic vertebral endplate comprising:
  i) an outer surface adapted to mate with a vertebral body,
  ii) an inner surface having a first articulation surface suitable for supporting articulation motion first thereon, and
  iii) a body portion connecting the inner and outer surfaces,
  iv) at least one sensor disposed within the body portion, and
b) a core member comprising:
  i) a first articulation surface suitable for supporting articulation motion.

In some embodiments, there is provided an intervertebral motion disc comprising:

a) a prosthetic vertebral endplate comprising:
  i) an outer surface adapted to mate with a vertebral body,
  ii) an inner surface having a first articulation surface suitable for supporting articulation motion first thereon, and
  iii) a body portion connecting the inner and outer surfaces, and
b) a core member comprising:
  i) a first articulation surface suitable for supporting articulation motion, and
  ii) at least one sensor.

In some embodiments, the at least one sensor (wherever located) comprises a plurality of sensors. In some embodiments, the sensor is adapted to transmit data. Preferably, the sensor is adapted to remotely transmit data. In some embodiments, the sensor is adapted to transmit data to a means for self actuation of the implant. In some embodiments, the endplate further comprises at least one sensor disposed within the body portion of the endplate, wherein the sensor is selected from the group consisting of a pressure sensor, a chemical sensor and a force sensor.

In some embodiments, the endplate further comprises a controller/processor disposed within the body portion of the endplate. In some embodiments, the endplate further comprises a battery disposed within the body portion of the endplate. In some embodiments, the endplate further comprises a piezo-electric element disposed within the body portion of the endplate.

The motion disc component of the present invention can be any prosthetic capable of restoring the natural motions of the intervertebral disc. In preferred embodiments, the motion disc is selected from the group consisting of an articulating disc, a cushion disc and a spring-based disc.

Preferred articulating motion devices are disclosed in U.S. Pat. Nos. 5,556,431 and 5,674,296, the specifications of which are incorporated by reference.

In some embodiments, the general structure of the articulating motion disc comprises:

a) a first prosthetic vertebral endplate comprising:
  i) an outer surface adapted to mate with a first vertebral body,
  ii) an inner surface having a first articulation surface,
  iii) a body portion connecting the inner and outer surfaces,
b) a second prosthetic vertebral endplate comprising:
  i) an outer surface adapted to mate with a second vertebral body, and
  ii) an inner surface comprising a first articulation surface,
c) a core member comprising:
  i) a first articulation surface adapted for articulation with the first articulation surface of the first endplate, and
  ii) a second articulation surface adapted for articulation with the first articulation surface of the second endplate, wherein the core member is oriented to produce a first articulation interface between the first articulation surface of the first endplate and the first articulation surface of the core member, and a second articulation interface between the first articulation surface of the second endplate and the second articulation surface of the core member.

In some embodiments, the general structure of the articulating motion disc is a two piece design and comprises:

a) a first prosthetic vertebral endplate comprising:
  i) an outer surface adapted to mate with a first vertebral body,
  ii) an inner surface having a first articulation surface,
  iii) a body portion connecting the inner and outer surfaces,
b) a second prosthetic vertebral endplate comprising:
  i) an outer surface adapted to mate with a second vertebral body, and
  ii) an inner surface comprising a second articulation surface, wherein the first and second articulation surfaces are oriented produce an articulation interface.

Preferably, the articulation interfaces form partial spheres.

The motion discs of the present invention can be adapted for use any of the lumbar, thoracic or cervical spine regions. In some embodiments wherein the motion disc is adapted for use in the lumbar region, the three-piece design having a core is selected. In some embodiments wherein the motion disc is adapted for use in the cervical region, the two-piece design is selected.

In some embodiments of the present invention, MEMS technology sensors and actuators may be incorporated into the device allowing the physician to make adjustments or gather data either automatically or telemetrically.

Figure 11:
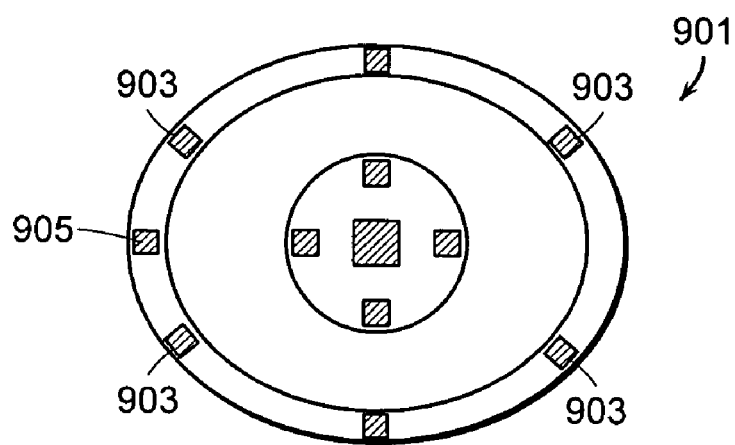
FIG. 11 is a top view of a core component of a three-piece motion device having a plurality of magnets embedded therein.

Now referring to FIG. 11, in one MEMS embodiment, the core component 901 of the prosthesis may be molded in such a way as to contain a plurality of magnets, including a plurality of symmetrical magnets 903 and an asymmetric locating magnet 905. The asymmetry provided by the asymmetric locating magnet could be predetermined by providing either an asymmetric location for a magnet (as shown) or by providing a different type of magnet (not shown), such as a different size or shape of magnet, or by reversing the polarity of one magnet in relation to the other magnets. In use, the relative position of the magnets could be ascertained while maintaining the current free floating articulating function of the core.

Figure 12:
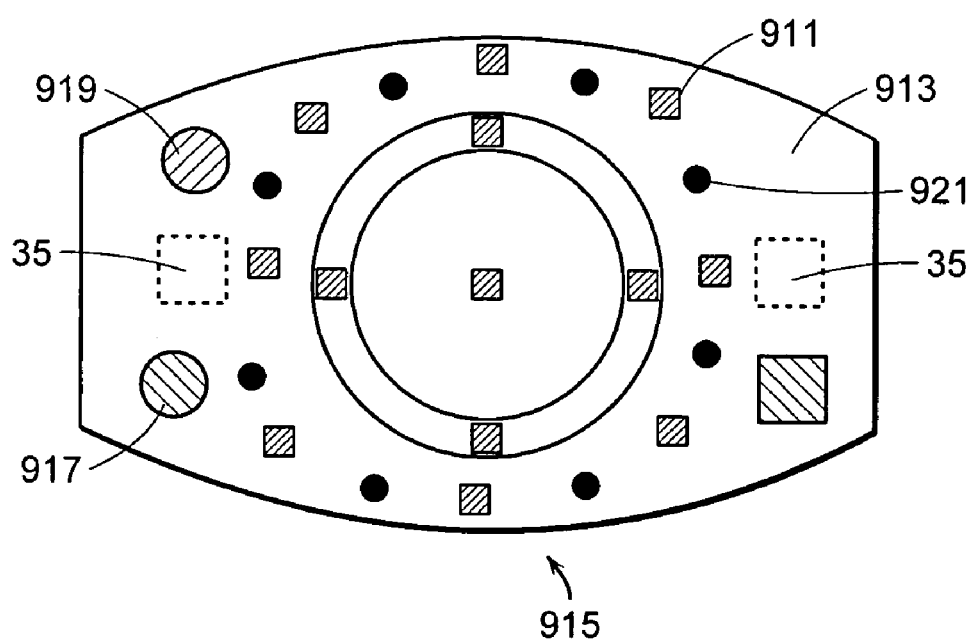
FIG. 12 is a top view of an inner plate of the present invention having various functional elements thereon.
Figure 13:
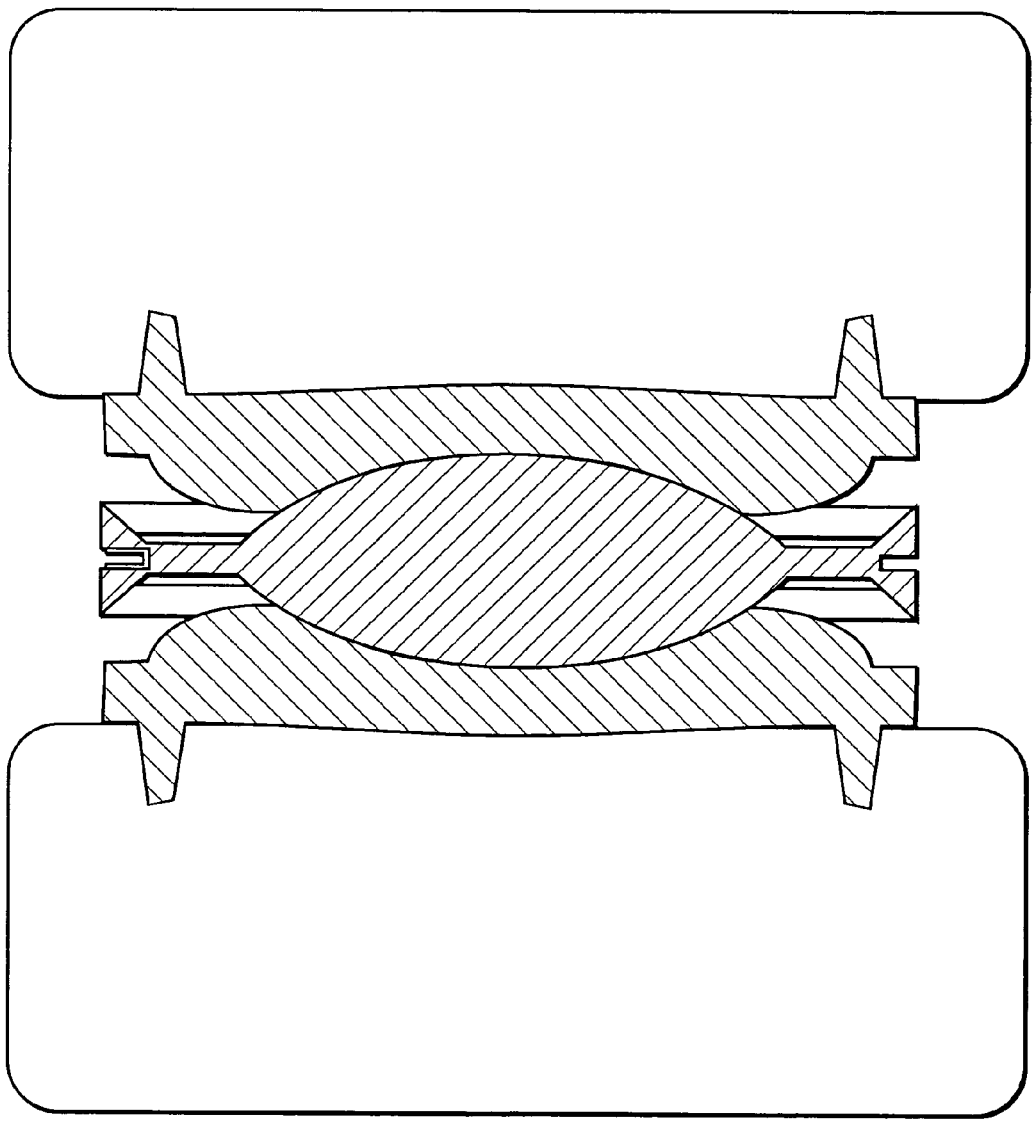
FIG. 13 is a cross-section of a conventional three-piece intervertebral articulating motion disc.

Now referring to FIG. 12, the magnetic fields created by the magnets of FIG. 11 could be detected by Hall Effect sensors 911 embedded near the inner surface 913 of the endplate 915. The signals produced thereby may be sent to a MEMS-type controller-processor 917 (also embedded near the inner surface of the plate). If adjustment were necessary, the controller/processor would then send a signal to a small motor (not shown) connected to or driving the adjustment screws to effect the desired adjustment.

In one aspect of the invention using Hall Effect sensors, there is provided in the core-endplate combination comprising at least one magnet in one of the components (the magnetic component), and at least one Hall Effect sensor in the other component (the sensor component). Preferably, there are at least two magnets in the magnetic component, and more preferably at least three magnets. In preferred embodiments, there are a plurality of magnets in the magnetic component arranged in a asymmetrical manner. Preferably, the sensor component does not have any magnets thereon.

In preferred embodiments, the prosthetic endplate is selected as the sensor component. This accommodates the need for robust circuitry needed to actuate the sensor and allows for thin film manufacturing techniques. Accordingly, the core component is preferably selected as the magnetic component.

In some embodiments using magnets, the core has oval or elliptical articulation surfaces. These shapes create partially constrained configurations that would prevent complete rotation of the core, a feature that would be desirable when embedded functional elements keyed to location are used. These non-spherical shapes may also generate different forces during different motions, which may be desirable for the distribution of loads during different motions. For example, if the anterior portion of an articulating surface were larger, its maximum load may be reduced during kyphotic motion.

In some embodiments, there is provided a magnetically-activated ratchet and pawl mechanism adapted to rotate the adjustment screws. Now referring to FIG. 14, In this embodiment, there is provided a pawl 801 having first 803 and second 805 end portions and a shaft 807 therebetween. An internal magnet 811 is connected to a first end of the pawl, while second end portion of the pawl defines a tooth 813 adapted for mating with corresponding teeth 815 located on a portion of the captured screw 817. Applying an external magnetic force (such as one from MRI 819) to the internal magnet causes linear movement of the internal magnet from a resting point to a stop point, thereby achieving an incremental rotation of the adjusting screw. The external magnet could then be turned off or reversed, and the internal magnet would return to its original position to repeat the cycle, if desired. This mechanism could be externally activated by a large magnet (such as an MRI), and may be more functionally robust than the application of rotational magnetic forces. In some embodiments, the pawl of FIG. 14 also includes an anti-backlash feature 818.

For a ratchet and pawl mechanism to rotate in either direction, a double ratchet design could be utilized with the teeth of the different ratchet pointing in opposite directions. The pawl mechanism can have a single arm or have a pair of arms, as shown in FIG. 15.

Figure 14:
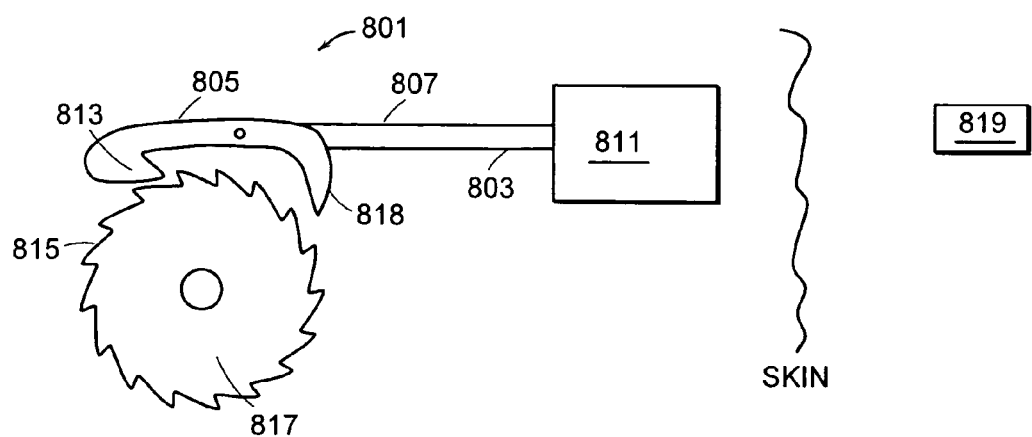
FIG. 14 is a depiction of a magnetically-activated ratchet and pawl mechanism adapted to rotate the adjustment screws of a motion disc.
Figure 15:
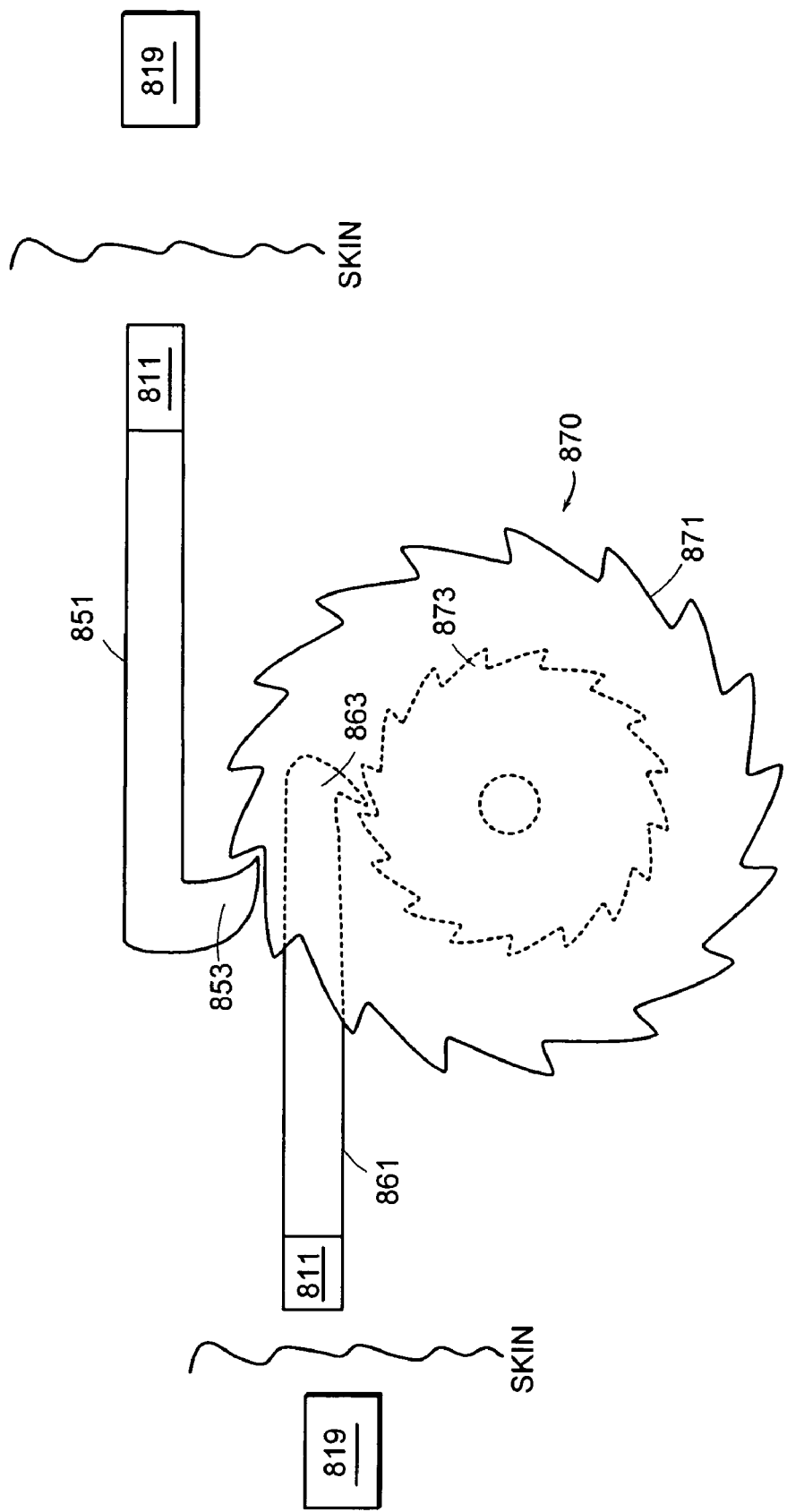
FIG. 15 is a depiction of a dual magnet ratchet and pawl mechanism adapted to rotate the adjustment screws of a motion disc.

Now referring to FIG. 15, in some embodiments, the ratchet and pawl mechanism of FIG. 14 is modified to contain a first pawl 851 having a first tooth 853, and a second pawl 861 having a second tooth 863 facing in a direction opposite to that of the first tooth. Likewise, the capture screw 870 comprises first 871 and second 873 ratchets located on a common axis and adapted to rotate upon the respective linear movement of the respective pawls.

Selective actuation of external magnets 819 upon opposed magnets 811 associated with the pawls allows selective rotation of the captured screw 817 in opposite directions. In FIG. 15, moving pawl 851 to the right results in clockwise actuation of the larger diameter wheel 871, while moving pawl 861 to the left results in counter-clockwise actuation of the smaller diameter wheel 871. In other embodiments (not shown), the ratchets have the same diameter. In some embodiments (not shown), the pawl arm is an integral body having opposed teeth so that magnetic attraction may more efficiently disengage the opposing pawl. However, there may also be a benefit to using a locking mechanism having separate pawl arms (as shown), as they prevent the desired rotation from occurring until the opposing pawl is released.

Figure 16:
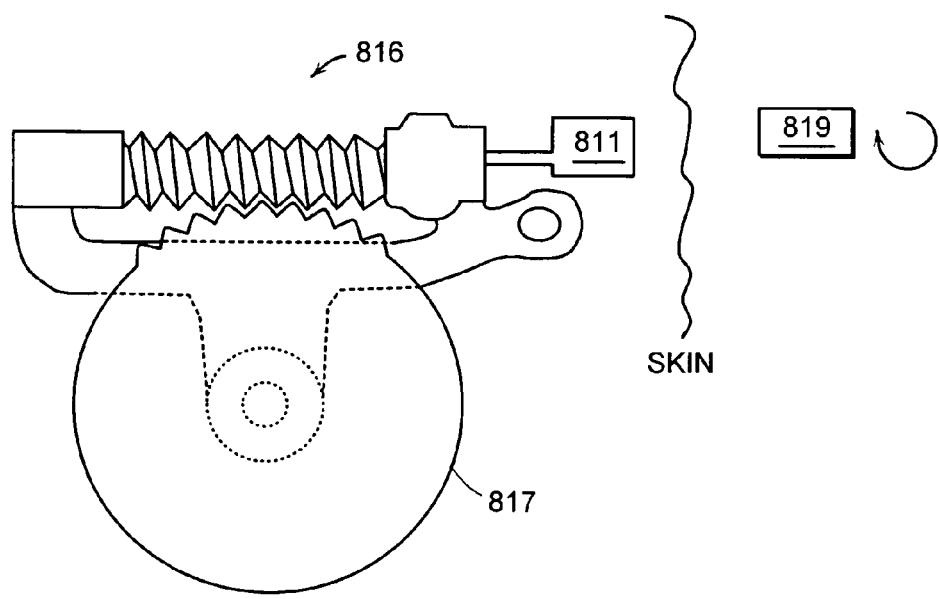
FIG. 16 is a depiction of a worm screw-driven adjustment mechanism of the present invention.

Now referring to FIG. 16, in another embodiment, a worm-screw 816 is coupled to a magnet 811 in order to drive pawl 817. In use, rotation of external magnet 819 causes rotation of internal magnet 811 which is coupled to the worm screw. Rotation could also be achieved by rotating a screw head via percutaneous access.

Therefore, in accordance with the present invention, there is provided an intervertebral motion disc comprising:
a) a prosthetic vertebral endplate component comprising:
   i) an outer surface adapted to mate with a vertebral body,
   ii) an inner surface having a first articulation surface suitable for supporting articulation motion first thereon, and
   iii) a body portion connecting the inner and outer surfaces, and
b) a core member component comprising:
   i) a first articulation surface suitable for supporting articulation motion,
wherein the articulation surfaces of the core and endplate are adapted to form an articulation interface, and wherein one of the components is a sensor component comprising a Hall Effect sensor, and the other component is a magnetic component comprising a magnet.

Energy for the electronics described above can be delivered from a battery, which could be recharged by transcutaneous Rf power transfer. Alternatively, at least one piezoelectric element could be incorporated to convert some of the natural mechanical forces present in the motion of a functional spinal unit into electrical energy, and to deliver that energy to the motor. Alternatively, the energy delivery device may be a capacitor.

Force and/or pressure sensors can be incorporated into the device to read the various forces on the device, and communicate that information via a wireless MEMS transmitter to a nearby external receiver. This would allow the physician to obtain real-time data on the function and performance of the implant, and prescribe adjustments or other therapy. In some embodiments, the sensor is a chemical sensor.

This data can then be directed from the external receiver into a database that is remotely viewed and acted upon by the surgeon over a secure internet connection with means described here within.

Since it is much easier to replace a core element of the three piece articulating motion disc than either endplate, in some embodiments, MEMS components shown earlier as being located upon an endplate component may alternatively be located in the core element.

It may also be desirable to implant pressure, chemical or force sensors in the local tissue surrounding the implant, including bone, annulus or surrounding muscle/ligamentous tissue. These sensors would be adapted to have direct communication, either by wires, mechanical coupling, or wireless communication, with a control unit of the motion disc prosthesis. Algorithms could be developed to effect an adjustment of the disc alignment to create an optimal load distribution based upon the forces sensed in the surrounding tissues.

Although the present invention was developed in response to a specific need associated with articulating motion discs, the present inventors believe that the concept developed herein may also be applicable to other orthopaedic implants that require precise positioning of two adjacent elements. Some such implants include, but are not limited to, spinal fusion, fusion of long bone fractures, alignment of severed tissue containing nerves (so as to promote regrowth, alignment of ducts, vessels, ligaments and tendons.

The sensors of the present invention may be used in many different spine related applications.

In some embodiments, the sensor is a force sensor adapted to measure a load transferred through the implant. The data compiled by such force sensors can then be used to determine various significant patient endpoints.

In one application in which a load sensor is used to measure loads through a fusion device, the load data can be used to determine the extent to which fusion has occurred through the fusion device. In preferred fusion-sensing embodiments, the sensor is located upon an internal surface of a fusion device and is adapted to measure bony apposition upon the sensor.

In one application in which a load sensor is used to measure loads through a spinal implant device, the load data can be used to determine the degree of load uniformity through the device. Preferably, the load uniformity sensor used to determine load uniformity is used in conjunction with a motion device. In another embodiment, the load data can be used to determine the degree of load uniformity at the interface between a prosthetic body and adjacent bone, thereby allowing the surgeon to determine whether bone resorption is occurring at that interface.

In some embodiments, the data from the force sensor can be correlated with a set of force ranges that could be expected to appear when certain physiologic phenomena occur. For example, the specific forces recorded by the sensor may enable the physician to determine that a specific negative outcome is occurring adjacent the sensor (such as prolonged inflammation, infection, bone resorption, or fibrous tissue growth) or that a specific positive outcome is occurring adjacent the sensor (such as bony deposition, bony ingrowth, reduction of force on a localized portion of an endplate, each of which could signal, for example, the desired progression of fusion).

In some embodiments, the sensor is a chemical sensor and is adapted to detect infection, inflammation, bone formation, or bone resorption.

In this embodiment, the sensor preferably comprises a bioMEMs device having a cantilever beam coated with a layer of material that is sensitive to high levels of chemicals or antibodies associated with either infection, inflammation, bone formation, or bone resorption. Preferably, the selected material is a binding partner molecule specific to the chemical, antigen or antibody associated with either infection, inflammation, bone formation, or bone resorption. In some embodiments, the layer is selected from the group consisting of an enzyme, a peptide, a protein, a polysaccharide, a nucleic acid, a carbohydrate, an antibody molecule, an antigen molecule, a pharmacological agent (such as a drug including a small organic molecule such as aspirin), a biopolymer, and a biochemical compound that reacts with one or more analytes or other biopolymers in a sample placed on the layer.

In some preferred embodiments, the chemical detector is adapted to detect single living cells, as disclosed in Example 2 of U.S. Pat. No. 6,289,717, the specification of which is incorporated by reference in its entirety herein.

In some embodiments, multiple sensors having different beam length or different coatings are used. Sensors having multiple beam lengths are expected to provide greater sensitivity, while sensors having different coatings are expected to provide greater specificity. In some embodiments, multiple sensors having substantial identical features are used in order to provide redundancy and robustness.

In embodiments wherein the sensor comprises a bioMEMs device having a cantilever beam coated with a layer of material that is sensitive to high levels of chemicals or antibodies associated with, inflammation, bone formation, or bone resorption, the layer of material may be sensitive to at least one protein selected from the group consisting of CSF-1, RANKL, TNF-alpha, and an interlukin (preferably, at least one of IL-6, IL-1 alpha and IL-1 beta. In some embodiments, the layer adapted to detect, inflammation, bone formation, bone resorption is a monoclonal antibody, and preferably is sensitive to TNF-alpha, and preferably is infliximab.

In preferred resorption-sensing embodiments, the sensor is located upon an external surface of the implant, and more preferably upon an external surface adapted to attach to bone.

In some embodiments, the sensor is adapted to determine a distance to a predetermined surface. In preferred embodiments thereof, this distance sensor is adapted to determine a distance to a surface on a polymer component. Preferably, the surface polymer component is adapted for articulation (and so preferably has a surface roughness Ra of no more than 50 um) and more preferably is made of polyethylene. In preferred embodiments thereof, the surgeon may use the change-in-distance data provided by the sensor to determine the extent of wear and/or deformation of the articulation polymer component. In other distance sensor embodiments, the articulation surface is made of a material selected from the group consisting of a metallic material (such as a titanium alloy, cobalt chromium and stainless steel), and a ceramic material (such as alumina, zirconia and mixtures thereof).

In some embodiments, the sensor is adapted to determine absorption of a specific wavelength of light by a specific volume of tissue. In preferred embodiments thereof, this light absorption sensor is adapted to determine absorption of light in the infrared spectrum. In preferred embodiments thereof, the surgeon may use the IR absorption data provided by the sensor to determine the extent of wear and/or deformation of an articulating polymer component. In preferred embodiments thereof, polymer debris particles that have infiltrated tissue adjacent to the articulating component will absorb the IR light, thereby providing a measure of wear at the articulating surface.

In some embodiments, the sensor is adapted to determine a distance to a change in temperature. In preferred embodiments thereof, the sensor comprises a memory metal rod that deflects in response to a temperature changes. The sensor is further adapted to measure and respond to a significant deflection of the memory metal rod. In preferred uses, the temperature sensor is adapted to detect infection (i.e., sense the rise in temperature associated with the immune response) and bone resorption (e.g., sense the rise in temperature associated with the phagocytic response to polyethylene wear debris). In preferred embodiments, the temperature sensor comprises a bimetal cantilever beam.

In other embodiments, the sensor of the present invention is adapted to provide data suitable to help determine implant location, implant geometry (such as height or width), implant integrity (such as wear, change in cross linking, hardness (by means of cantilever deflection).

In some embodiments, the sensor is located upon an external surface of the implant, and more preferably upon an external surface adapted to attach to bone. In preferred embodiments thereof, this surface-based sensor is adapted to sense at least one phenomenon selected from the group consisting of inflammation, temperature, infection, bone resorption, bone formation and bone deposition.

In some embodiments, the sensor is a sensor adapted to trigger the actuation of an actuator.

In one embodiment, the sensor is adapted to sense a change in the patient's local environment and then actuate a fluid reservoir in response thereto. For example, in one preferred embodiment, the sensor is adapted to sense a change in the patient's local environment and then actuate a fluid reservoir in response thereto. In an especially preferred embodiment, the sensor is associated with an implant comprising a housing containing a therapeutic fluid (such as a drug), wherein an opening in the housing is covered by a meltable cover (such as a gold leaf or a thermoplastic). Upon sensing a significant change in environment, the sensor actuates a heater that heats the meltable cover to its melting point, thereby locally releasing the therapeutic fluid. In preferred embodiments, the implant associated with this sensor is selected from the group consisting of a fusion device (such as a cage), a motion disc (such as an articulating disc), posterior fixation devices, and anterior fixation devices.

In some preferred embodiments related to release of therapeutic drugs, the sensor is adapted to sense the presence of at least one compound associated with inflammation. In preferred embodiments thereof, this inflammation sensor is adapted to sense the presence of an inflammatory marker associated with degenerative disc disease or the degeneration of a facet joint (markers associated with osteoarthritis). In preferred embodiments thereof, this inflammation sensor is adapted to sense the presence of an inflammatory marker selected from the group consisting of an MMP, TNF-alpha, and an interleukin.

In some preferred embodiments related to release of therapeutic drugs, the sensor is adapted to sense the presence of at least one compound associated with bone resorption. In preferred embodiments thereof, this bone resorption sensor is adapted to sense the presence of an inflammatory marker selected from the group consisting of an MMP, TNF-alpha, and an interleukin.

In some preferred embodiments related to release of therapeutic drugs, the sensor is adapted to sense the presence of at least one compound associated with infection. In preferred embodiments thereof, this infection sensor is adapted to sense the presence of a microbe. In preferred embodiments thereof, this infection sensor is adapted to sense the presence of a microbe selected from the group consisting of *staph. aureus* and *staph. epidermis*. In preferred embodiments thereof, this infection sensor is adapted to trigger an actuator releasing an anti-microbial fluid, preferably an antibiotic.

As above, in some embodiments, multiple sensors may be provided in order to provide enhanced sensitivity, enhanced specificity or redundancy (providing robustness).

In one embodiment, the sensor is adapted to sense a change in the patient's local environment and then actuate a motor or gear in response thereto. For example, in one preferred embodiment, the sensor is adapted to sense a change in the patient's local environment and then actuate a gear in order to change the location or orientation of a prosthetic component.

In an especially preferred embodiment, the sensor is associated with an implant adapted to treat scoliosis, wherein the implant comprises an expandable rod. Upon sensing a significant change in environment, the sensor actuates a gear associated with the expandable rod, thereby increasing the length of the rod.

In an especially preferred embodiment, the sensor is associated with an implant adapted to adjust the center of rotation of an articulating motion disc. Upon sensing a significant change in environment, the sensor actuates a gear or linear motor associated with an inner plate of a prosthetic endplate, thereby adjusting the relative position of the inner plate vis-a-vis the its associated outer plate.

In some embodiments, the sensors and actuators are selected from the sensors and actuators disclosed in Published U.S. Patent Application No. 2003/0028036; 2002/0006682; 2002/0139171; 2002/0170875; 2002/0174724; 2003/0062579; 2003/0116813; 2004/0021184, the specifications of which are incorporated by reference in its entirety.

In some embodiments, the sensors and actuators discloses in Roy et al., *Neurosurgery* 2001 October 49(4): 779-97; are selected.

In some embodiments, the sensor is selected from the ionic polymer sensors disclosed in U.S. Pat. No. 6,475,639, and in Published U.S. Patent Application No. 2002/0039620 ("Shahinpoor"), the specifications of which are incorporated by reference in its entirety.

In some embodiments, the sensor is selected from the sensors disclosed in U.S. Pat. Nos. 6,436,346; 6,336,366; 6,311,557; 6,311,549; 6,289,717; 6,263,736; 6,212,939; 6,167,748; 6,118,124; 6,096,559; 6,050,722; 6,016,686; 5,719,324 and 5,445,008, and in Published U.S. Patent Application No. 2001/0028036.

In some embodiments, the sensor is selected from the sensors disclosed in U.S. Pat. No. 6,447,448 ("Ishikawa"), the specification of which is incorporated by reference in its entirety.

In some embodiments, the sensor is used with a drug delivery device disclosed in U.S. Pat. No. 6,352,524 ("Bunt"), the specification of which is incorporated by reference in its entirety.

In some embodiments, the sensor of the present invention is associated with actuation means for activating an actuator associated with the implant. In some embodiments, the sensor of the present invention is associated with data transmission means for transmitting the information produced by the sensor to a receiver located, in some embodiments, within the patient, and in other embodiments, outside the patient.

Figure 17:
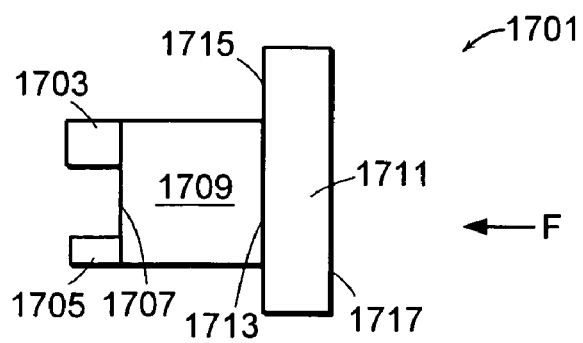
FIG. 17 is represents a preferred force or pressure sensor of the present invention.

Now referring to FIG. 17, there is provided a preferred force or pressure sensor 1701 of the present invention. The sensor comprises a light source 1703 and a light detector 1705 disposed on a first side 1707 of a wave guide 1709, and a deformable dielectric or reflective layer 1711 having a first side 1715 and a second side 1717, the first side of the deformable layer disposed on a second side 1713 of the wave guide. The deformable layer deforms a predetermined amount in response to forces directed against its second side, thereby altering the path traveled through the wave guide. In use, the light source emits light which travels through the wave guide. The light is then reflected back into the wave guide at an angle determined by the extent of deformation of deformable layer 1711. The light detector then registers the change in the light pattern caused by the deformation.

Figure 18:
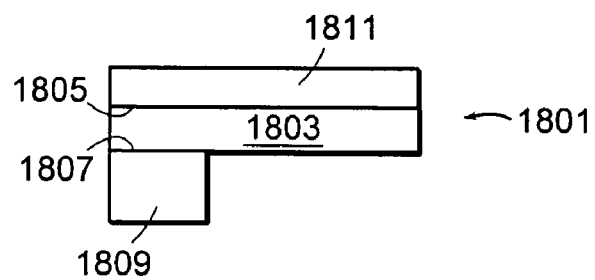
FIG. 18 is represents a preferred chemical sensor of the present invention.

Now referring to FIG. 18, there is provided a preferred chemical sensor 1801 of the present invention. The sensor comprises a cantilever beam 1803 having a first side 1805 and a second side 1807; a consumable coating 1811 disposed on the first side of the cantilever beam, and a detector 1809 disposed on the second side of the cantilever beam. The consumable coating has sufficient thickness to affect the mechanical response of the cantilever beam. For example, the coating may be adapted to increase the effective stiffness of the beam. In use, the presence of a target chemical compound causes a chemical reaction with the consumable coating to occur, thereby decreasing the thickness of the coating. The corresponding change in the deflection of the cantilever beam is registered by the detector.

Figure 19:
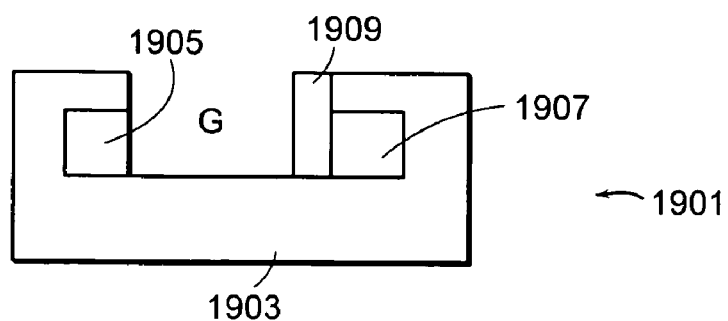
FIG. 19 is represents a preferred optical sensor of the present invention.

Now referring to FIG. 19, there is provided a preferred optical sensor 1901 of the present invention. The sensor comprises a housing 1903 having a light source 1905 and a light detector 1907, wherein the light source and light detector are separated by a gap G. The light detector is adapted to detect changes in the extent to which media in the gap absorbs light from the light source. For example, in use, the light source can be an IR source, and the light detector can be adapted to detect the presence of polyethylene wear particles that have infiltrated the gap and have absorbed IR light emitted by the light source. In some embodiments, a light filter 1909 is disposed between the light source and a light detector.

In some embodiments, the sensor is located within the bulk of an implant. In some embodiments, the sensor is placed upon a surface of the implant. These surface—located sensors are advantageously used in situations wherein the load, force or chemical constituent at a surface is of importance. In some embodiments, the sensor is placed in a location in the patient's tissue.

In some embodiments directed at monitoring bone formation, the sensor is a chemical sensor adapted to detect local concentrations of a constituent associated with bone formation or resorption. In some embodiments, the constituent may be an ion, preferably selected from the group consisting of phosphate, calcium, magnesium, carbonate, and sulfate ions. In some embodiments, the constituent may be an growth factor, preferably selected from the group consisting of a BMP, CDMP, TGF, PDGF and VEGF. In some embodiments, the constituent may be an enzyme. In some embodiments, the constituent may be an inflammatory mediator, preferably selected from the group consisting of TNF-a, an MMP and an interleukin. In some embodiments, the constituent may be a cell, preferably selected from the group of bone-forming cells (such as osteoblasts and stem cells) and a scar forming cell (such as a fibroblast). Preferably, the implant carrying the bone detecting sensor may be equipped with feedback electronics and an actuator that responds to the presence or absence of a constituent associated with bone, preferably by releasing a bone forming agent. For example, if the chemical sensor detected a relative absence of osteoblasts (or the relative abundance of fibroblasts) in a region in which bone is desired, it could signal an actuator (such as a pump) to release a bone-forming substance such as a BMP or a CDMP into the region of concern.

In some embodiments, the implant comprises a first chemical sensor and a second sensor selected from the group consisting of a force sensor and a load sensor. Such an implant would be especially equipped to monitor bony integration of the implant surface to local bone. In one case, the force or load sensor could monitor the extent of bony apposition while the chemical sensor could monitor the presence of absence of bone-related constituents.

We claim:

1. A prosthetic endplate in an intervertebral motion disc having an anterior end and a posterior end, the endplate comprising:
   i) an outer plate comprising an outer surface adapted for fixation to a first vertebral body, an inner surface, and a body portion therebetween,
   ii) an inner plate comprising an outer surface having a first articulation surface, an inner surface, and a body portion therebetween,
   iii) means for selectively adjusting a relative position of the inner plate upon the outer plate,
   wherein the means for selectively adjusting a relative position is disposed upon the inner surfaces and comprises an elongated channel and an elongated projection adapted to mate with the elongated channel,
   wherein the elongated projection comprises a threaded throughhole running in the direction of the elongation,
   wherein the means for selectively adjusting a relative position further comprises a captured screw disposed within the throughhole, the screw having an elongated shaft and a threadform thereon, the threadform being complimentary to the threaded throughhole,
   wherein the elongated channel comprises means for capturing the screw,
   wherein the screw comprises a blunt distal tip, and a proximal head having a slot, the elongated shaft comprising a recess adapted for reception of a locking clip, a locking clip received in the recess of the elongated shaft, wherein the means for capturing the screw comprises an anterior recess and a posterior recess defined by necks in the elongated channel, wherein the blunt distal tip and the proximal head of the screw are respectively seated in the anterior recess and the posterior recess to render the screw captured and spatially fixed save rotation, wherein said selectively adjusting a relative position of the inner plate upon the outer plate comprises radially translating the inner plate relative to the outer plate.

2. The endplate of claim 1 wherein the elongated channel is formed upon the inner surface of the outer plate and the elongated projection is formed upon the inner surface of the inner plate.

3. The endplate of claim 1 wherein the elongated channel is formed upon the inner surface of the inner plate and the projection is formed upon the inner surface of the outer plate.

4. The endplate of claim 1 wherein the head of the screw is selected from the group consisting of a slotted head, an Allen head, a Torx.sup.R head, a Phillips head, and a Robertson.sup.R head.

5. The endplate of claim 1 wherein the screw further comprises a magnetic portion.

6. The endplate of claim 1 further comprising: iv) a locking means for locking the screw.

7. The endplate of claim 6 wherein the locking means comprises a cam.

8. The endplate of claim 6 wherein the locking means comprises a hinged lever.

9. The endplate of claim 6 wherein the locking means comprises a screw.

10. The endplate of claim 1 wherein the elongated projection runs in the anterior-posterior direction.

* * * * *